(12) United States Patent
Zhang et al.

(10) Patent No.: US 11,970,723 B2
(45) Date of Patent: Apr. 30, 2024

(54) STRAIN PRODUCING D-ALLULOSE 3-EPIMERASE AND APPLICATION THEREOF

(71) Applicant: Jiangnan University, Wuxi (CN)

(72) Inventors: Tao Zhang, Wuxi (CN); Mengying Hu, Wuxi (CN); Bo Jiang, Wuxi (CN); Mengli Li, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/187,984

(22) Filed: Mar. 22, 2023

(65) Prior Publication Data

US 2023/0265411 A1    Aug. 24, 2023

Related U.S. Application Data

(63) Continuation of application No. PCT/CN2022/092360, filed on May 12, 2022.

(30) Foreign Application Priority Data

Dec. 2, 2021 (CN) .......................... 202111457416.2

(51) Int. Cl.
    *C12N 9/90* (2006.01)
    *C12N 15/75* (2006.01)
(52) U.S. Cl.
    CPC .............. *C12N 9/90* (2013.01); *C12N 15/75* (2013.01)
(58) Field of Classification Search
    CPC . C12N 9/90; C12N 15/75; C12N 9/16; C12N 9/88; C12N 15/70; C12N 15/67; C12N 15/74; C12P 19/02; C12P 19/24
    See application file for complete search history.

(56) References Cited

FOREIGN PATENT DOCUMENTS

| CN | 104894047 A | 9/2015 |
| CN | 112695006 A | 4/2021 |
| CN | 113249287 A | 8/2021 |
| CN | 114350699 A | 4/2022 |
| WO | 2019144944 A1 | 8/2019 |

OTHER PUBLICATIONS

Wen, Yuwei et al. "Heterologous Expression and Enzymatic Characterization ofD-Psicose 3-Epimerase" Journal of Food Science and Biotechnology. vol. 3,Issue 37. p. 289-295. Mar. 15, 2018.

Chen, Jinqi et al. "High-level intra- and extra-cellular production of d-psicose 3-epimerase via a modified kylose-inducible expression system in Bacillus subtilis" J. Ind Microbiol Biotechnol. Aug. 20, 2016, V11, Issue 43.

*Primary Examiner* — Iqbal H Chowdhury
(74) *Attorney, Agent, or Firm* — IPRO, PLLC (57) ABSTRACT

The present disclosure discloses a strain producing D-allulose 3-epimerase and application thereof, and belongs to the technical field of bioengineering. The present disclosure provides a method for improving the expression of D-allulose 3-epimerase by screening promoters and optimizing RBS thereof. The recombinant *Bacillus subtilis* constructed using thevectors pP43NMK-hag and pP43NMK-hag-RBS4 provided by the present disclosure improves the enzyme activity of a target gene D-allulose 3-epimerase, and theenzyme activities in shake flasks upon transformation are 1.30 times and 1.69 times that of an original vector. The present disclosure further provides a non-antibiotic resistance vector and a non-antibiotic resistance recombinant *B. subtilis* strain. Using the non-antibiotic resistance strain *B. subtilis* 1A751-dal-/pP43NMK-hag-RBS4-dpe-dal provided by the present disclosure, the highest fermentation enzyme activity in a shake flask is 24.72 U/mL, and the enzyme activity in a fermenter is 714.8 U/mL.

4 Claims, 2 Drawing Sheets

Specification includes a Sequence Listing.

SEQUENCE LISTING

```
Sequence total quantity: 23
SEQ ID NO: 1            moltype = DNA  length = 870
FEATURE                 Location/Qualifiers
source                  1..870
                        mol_type = other DNA
                        organism = synthetic construct
SEQUENCE: 1
atgaagcatg gtatttatta cgcgtactgg gaacaggaat gggcagcaga ttacaagcgg   60
tatgtagaga aggcggcaaa gcttggattc gatatactgg aggttggcgc ggcgccactg  120
ccggactatt ctgcgcagga ggtaaaggaa ctgaaaaaat gcgccgatga taacggtatc  180
cagctgaccg cgggatatgt tcccgccttc aatcataaca tggttcctc agatccgaag  240
atcagggaag aggcgcttca atggtataaa cgcctgttcg aggtgatggc aggccttgat  300
attcatctga ttggcggagc gctttattca tactggccgg tggactttgc cacagccaat  360
aaggaagagg actggaagca cagcgtggag ggaatgcaga ttctggcgcc catcgccagc  420
cagtatggca tcaatctggg aatggaagtc ctgaaccgct ttgagagcca tatcttaaat  480
acttcggaag aaggcgtgaa gttcgtgacg gaagtaggca tggataatgt gaaagtcatg  540
ctggatacgt tccacatgaa catcgaggaa tcgagcattg gcgacgcgat ccgccatgcc  600
gggaaacttc ttggacactt ccacaccggc gagtgcaacc gcatggtacc cggaaagggc  660
cgcaccccat ggagggagat cggggatgcc ttgcgcgaga ttgagtatga cggaaccgtg  720
gttatggagc catttgtacg catgggcgga caggtaggct ctgatatcaa ggtctggaga  780
gacatcagca agggcgcggg agaggaccgg ctggatgagg atgcaaggcg cgcggtagag  840
ttccagagat acatgcttga atggaagtaa                                   870

SEQ ID NO: 2            moltype = DNA  length = 144
FEATURE                 Location/Qualifiers
source                  1..144
                        mol_type = other DNA
                        organism = synthetic construct
SEQUENCE: 2
ggatttttt attttgtat taacaaaatc agagacaatc cgatattaat gatgtagccg    60
ggaggaggcg caaaagactc agccagttac aaaataaggg cacaaggacg tgccttaaca  120
acatattcag ggaggaacaa aaca                                         144

SEQ ID NO: 3            moltype = DNA  length = 103
FEATURE                 Location/Qualifiers
source                  1..103
                        mol_type = other DNA
                        organism = synthetic construct
SEQUENCE: 3
acttctcaaa gatcccatgt gcttaaaatt aaagtttaaa tatttggatt ttttaaataa   60
agcgtttaca atatatgtag aaacaacaaa gggggagatt tgt                    103

SEQ ID NO: 4            moltype = DNA  length = 446
FEATURE                 Location/Qualifiers
source                  1..446
                        mol_type = other DNA
                        organism = synthetic construct
SEQUENCE: 4
ggatttttt attttgtat taacaaaatc agagacaatc cgatattaat gatgtagccg    60
ggaggaggcg caaaagactc agccagttac aaaataaggg cacaaggacg tgccttaaca  120
acatattcag ggaggaacaa aacaggatcc tgataggtg tatgttttcg cttgaacttt   180
taaatacagc cattgaacat acggttgatt taataactga caaacatcac cctcttgcta  240
aagcggccaa ggacgctgcc gccggggctg tttgcgtttt tgccgtgatt tcgtgtatca  300
ttggtttact tattttttg ccaaagctgt aatggctgaa aattcttaca tttattttac   360
atttttagaa atgggcgtga aaaaagcgc gcgattatgt aaaatataaa gtgatagcgg   420
tacctcgag aaaaggagga aaaaaa                                        446

SEQ ID NO: 5            moltype = DNA  length = 206
FEATURE                 Location/Qualifiers
source                  1..206
                        mol_type = other DNA
                        organism = synthetic construct
SEQUENCE: 5
acttctcaaa gatcccatgt gcttaaaatt aaagtttaaa tatttggatt ttttaaataa   60
agcgtttaca atatatgtag aaacaacaaa gggggagatt tgtacttctc aaagatccca  120
tgtgcttaaa attaaagttt aaatatttgg attttttaaa taaagcgttt acaatatatg  180
tagaaacaac aaagggggag atttgt                                       206
```

```
SEQ ID NO: 6            moltype = DNA  length = 288
FEATURE                 Location/Qualifiers
source                  1..288
                        mol_type = other DNA
                        organism = synthetic construct
SEQUENCE: 6
ggattttttt attttgtat  taacaaaatc agagacaatc cgatattaat gatgtagccg   60
ggaggaggcg caaaagactc  agccagttac aaaataaggg cacaaggacg tgccttaaca  120
acatattcag ggaggaacaa  aacaggattt ttttattttt gtattaacaa aatcagagac  180
aatccgatat taatgatgta  gccgaggagga ggcgcaaaag actcagccag ttacaaaata  240
agggcacaag gacgtgcctt  aacaacatat tcagggagga acaaaaca              288

SEQ ID NO: 7            moltype = DNA  length = 328
FEATURE                 Location/Qualifiers
source                  1..328
                        mol_type = other DNA
                        organism = synthetic construct
SEQUENCE: 7
ggcggcgttc tgtttctgct  tcggtatgtg attgtgaagc tggcttacag aagagcggta   60
aaagaagaaa taaaaagaaa  atcatctttt ttgtttggaa agcgagggaa gcgttcacag  120
tttcgggcag cttttttat   aggaacattg atttgtattc actctgccaa gttgttttga  180
tagagtgatt gtgataattt  taaatgtaag cgttaacaaa atttctccagt cttcacatcg  240
gtttgaaagg aggaagcgga  agaatgaagt aagagggatt tttgactccg aagtaagtct  300
tcaaaaaatc aaataaggag  tgtcaaga                                    328

SEQ ID NO: 8            moltype = DNA  length = 625
FEATURE                 Location/Qualifiers
source                  1..625
                        mol_type = other DNA
                        organism = synthetic construct
SEQUENCE: 8
agctgggtaa agcctatgaa  ttctccattt tcttctgcta tcaaaataac agactcgtga   60
ttttccaaac gagctttcaa  aaaagcctct gcccccttgca aatcggatgc ctgtctataa  120
aattcccgat attggttaaa  cagcggcgca atggcggccg catctgatgt ctttgcttgg  180
cgaatgttca tcttatttct  tcctccctct caataatttt tcattctat ccctttctg    240
taaagtttat ttttcagaat  acttttatca tcatgctttg aaaaaatatc acgataaatt  300
ccattgttct cacggaagca  cacgcaggtc atttgaacga attttttcga caggaatttg  360
ccgggactca ggagcatttta  acctaaaaaa gcatgacatt tcagcataat gaacatttac  420
tcatgtctat tttcgttctt  ttctgtatga aaatagttat ttcgagtctc tacggaaata  480
gcgagagatg atatacctaa  atagagataa aatcatctca aaaaaatggg tctactaaaa  540
tattattcca tctattacaa  taaattcaca gaatagtctt ttaagtaagt ctactctgaa  600
ttttttttaaa aggagagggt  aaaga                                      625

SEQ ID NO: 9            moltype = DNA  length = 128
FEATURE                 Location/Qualifiers
source                  1..128
                        mol_type = other DNA
                        organism = synthetic construct
SEQUENCE: 9
cagaaagcag acggacaccg  cgatccgcct gcttttttta gtggaaacat acccaatgtg   60
ttttgtttgt ttaaaagaat  tgtgagcggg aatacaacaa ccaacaccaa ttaaaggagg  120
aattcaaa                                                           128

SEQ ID NO: 10           moltype = DNA  length = 272
FEATURE                 Location/Qualifiers
source                  1..272
                        mol_type = other DNA
                        organism = synthetic construct
SEQUENCE: 10
tactacctgt cccttgctga  tttttaaacg agcacgagag caaaaccccc ctttgctgag   60
gtggcagagg gcaggttttt  ttgtttcttt tttctcgtaa aaaaaagaaa ggtcttaaag  120
gttttatggt tttggtcggc  actgccgaca gcctcgcaga gcacacactt tatgaatata  180
aagtatagtg tgttatactt  tacttggaag tggttgccgg aaagagcgaa aatgcctcac  240
atttgtgcca cctaaaaagg  agcgatttac at                              272

SEQ ID NO: 11           moltype = DNA  length = 569
FEATURE                 Location/Qualifiers
source                  1..569
                        mol_type = other DNA
                        organism = synthetic construct
SEQUENCE: 11
cagcagttct tttccgtcct  ctcttaagta agcgctggtg aagtttgttg attgcacctg   60
gtgaataagt tcaacagaca  ctcccgccag cagcacaatc gcaatataa cacccgccaa  120
gaacattgtg cgctgccggt  ttattttggg atgatgcaa aaaagatata agcccgacag  180
aacaacaatt gaccattgaa  tcagcagggt gctttgtctg cttaatataa aataacgttc  240
gaaatgcaat acataatgac  tgaataactc caacacgaac aacaatcctt tacttcttat  300
taaggcctca ttcggttaga  cagcggactt ttcaaaagt ttcaagatga acaaaaata   360
tctcatcttc cccttgatat  gtaaaaaaca taactcttga atgaaccacc acatgacact  420
tgactcatct tgatattatt  caacaaaaac aaacacagga caatactatc aattttgtct  480
```

```
agttatgtta gttttttgttg agtattccag aatgctagtt taatataaca atataaagtt    540
ttcagtattt tcaaaaaggg ggatttatt                                        569

SEQ ID NO: 12          moltype = DNA   length = 300
FEATURE                Location/Qualifiers
source                 1..300
                       mol_type = other DNA
                       organism = synthetic construct
SEQUENCE: 12
taaaaatatc gtggaagccc acaacggatc aattactgtg cacagccgaa tagataaagg      60
aacaacattt tcttttttata ttccgacaaa acggtaaaat cgagtctgaa tttgccgaag    120
aatcttgttc cataagaaac acccgctgac tgagcgggtg ttttttttaat agccaacatt   180
aataaaattt aaggatatgt taatataaat tcccttccaa attccagtta ctcgtaatat    240
agttgtaatg taacttttca agctattcat acgacaaaaa agtgaacgga ggggtttcaa    300

SEQ ID NO: 13          moltype = DNA   length = 446
FEATURE                Location/Qualifiers
source                 1..446
                       mol_type = other DNA
                       organism = synthetic construct
SEQUENCE: 13
ggatcctgat aggtggtatg ttttcgcttg aacttttaaa tacagccatt gaacatacgg      60
ttgatttaat aactgacaaa catcaccctc ttgctaaagc ggccaaggac gctgccgccg    120
gggctgtttg cgttttttgcc gtgatttcgt gtatcattgg tttacttatt ttttttgccaa  180
agctgtaatg gctgaaaatt cttacattta ttttacattt ttagaaatgg gcgtgaaaaa    240
aagcgcgcga ttatgtaaaa tataaagtga tagcggtacc ctcgagaaaa ggaggaaaaa    300
aaggattttt ttatttttgt attaacaaaa tcagagacaa tccgatatta atgatgtagc    360
cgggaggagg cgcaaaagac tcagccagtt acaaaataag ggcacaagga cgtgccttaa    420
caacatattc agggaggaac aaaaca                                          446

SEQ ID NO: 14          moltype = DNA   length = 247
FEATURE                Location/Qualifiers
source                 1..247
                       mol_type = other DNA
                       organism = synthetic construct
SEQUENCE: 14
acttctcaaa gatcccatgt gcttaaaatt aaagtttaaa tatttggatt ttttaaataa      60
agcgtttaca atatatgtag aaacaacaaa gggggagatt tgtggatttt tttattttttg   120
tattaacaaa atcagagaca atccgatatt aatgatgtag ccgggaggag cgcaaaaga    180
ctcagccagt tacaaaataa gggcacaagg acgtgcctta acaacatatt cagggaggaa    240
caaaaca                                                              247

SEQ ID NO: 15          moltype = DNA   length = 247
FEATURE                Location/Qualifiers
source                 1..247
                       mol_type = other DNA
                       organism = synthetic construct
SEQUENCE: 15
ggatttttttt attttttgtat taacaaaatc agagacaatc cgatattaat gatgtagccg     60
ggaggaggcg caaaagactc agccagttac aaaataaggg cacaaggacg tgccttaaca    120
acatattcag ggaggaacaa aacaacttct caaagatccc atgtgcttaa aattaaagtt    180
taaatatttg gattttttaa ataaagcgtt tacaatatat gtagaaacaa caagggggga    240
gatttgt                                                              247

SEQ ID NO: 16          moltype = DNA   length = 405
FEATURE                Location/Qualifiers
source                 1..405
                       mol_type = other DNA
                       organism = synthetic construct
SEQUENCE: 16
acttctcaaa gatcccatgt gcttaaaatt aaagtttaaa tatttggatt ttttaaataa      60
agcgtttaca atatatgtag aaacaacaaa gggggagatt tgtggatcct gataggtggt    120
atgtttttcgc ttgaactttt aaatacagcc attgaacata cggttgattt aataactgac    180
aaacatcacc ctcttgctaa agcggccaag gacgctgccg ccggggctgt ttgcgttttt    240
gccgtgattt cgtgtatcat tggtttactt atttttttgc caaagctgta atggctgaaa    300
attcttacat ttatttttaca ttttttagaaa tgggcgtgaa aaaaagcgcg cgattatgta    360
aaatataaag tgatagcggt accctcgaga aaaggaggaa aaaaa                     405

SEQ ID NO: 17          moltype = DNA   length = 405
FEATURE                Location/Qualifiers
source                 1..405
                       mol_type = other DNA
                       organism = synthetic construct
SEQUENCE: 17
ggatcctgat aggtggtatg ttttcgcttg aacttttaaa tacagccatt gaacatacgg      60
ttgatttaat aactgacaaa catcaccctc ttgctaaagc ggccaaggac gctgccgccg    120
gggctgtttg cgttttttgcc gtgatttcgt gtatcattgg tttacttatt ttttttgccaa  180
agctgtaatg gctgaaaatt cttacattta ttttacattt ttagaaatgg gcgtgaaaaa    240
aagcgcgcga ttatgtaaaa tataaagtga tagcggtacc ctcgagaaaa ggaggaaaaa    300
```

```
aaacttctca aagatcccat gtgcttaaaa ttaaagttta aatatttgga ttttttaaat    360
aaagcgttta caatatatgt agaaacaaca aagggggaga tttgt                   405

SEQ ID NO: 18          moltype = DNA   length = 604
FEATURE                Location/Qualifiers
source                 1..604
                       mol_type = other DNA
                       organism = synthetic construct
SEQUENCE: 18
ggatcctgat aggtggtatg ttttcgcttg aacttttaaa tacagccatt gaacatacgg    60
ttgatttaat aactgacaaa catcaccctc ttgctaaagc ggccaaggac gctgccgccg   120
gggctgtttg cgttttttgcc gtgatttcgt gtatcattgg tttacttatt ttttgccaa   180
agctgtaatg gctgaaaatt cttacattta ttttacattt ttagaaatgg gcgtgaaaaa   240
aagcgcgcga ttatgtaaaa tataaagtga tagcggtacc ctcgagaaaa ggaggaaaaa   300
aaggatcctg ataggtggta tgttttcgct tgaacttttaa aatacagcca ttgaacatac   360
ggttgattta ataactgaca acatcaccc tcttgctaaa gcggccaagg acgctgccgc    420
cggggctgtt tgcgttttg ccgtgatttc gtgtatcatt ggtttactta ttttttgcc    480
aaagctgtaa tggctgaaaa ttcttacatt tattttacat tttagaaat gggcgtgaaa    540
aaaagcgcgc gattatgtaa aatataaagt gatagcggta ccctcgagaa aaggaggaaa   600
aaaa                                                               604

SEQ ID NO: 19          moltype = DNA   length = 1167
FEATURE                Location/Qualifiers
source                 1..1167
                       mol_type = other DNA
                       organism = synthetic construct
SEQUENCE: 19
atgagcacaa aaccttttta cagagatacg tgggcggaaa ttgacttgtc cgcgataaag    60
gaaaatgtca gcaatatgaa aaaacatatc ggtgaacatg tccacttgat ggcagttgtg   120
aaagcaaacg cctacgggca tggtgatgca gaaacagcaa aggctgctct tgacgcaggt   180
gcttcatgct tggccgttgc cattttggat gaagcgattt cactgcgcaa aaagggattg   240
aaggcgccta tattggtgct tggcgcggtt ccccgggagt atgtggcaat cgctgctgag   300
tatgacgtga ccttaacagg ttattctgtt gaatggcttc aggaggcagc cgccacacg    360
aaaaaaggtt ctcttcattt tcatctgaag gtcgatacgg ggatgaacag acttggtgta   420
aaaacagagg aagaagttca gaacgtgatg gcaattcttg accgcaaccc tcgtttaaag   480
tgcaaagggg tatttaccca ttttgcgaca gcggatgaaa aagaaagagg ctatttctta   540
atgcagtttg agcgctttaa agagctgatt gctccgctgc cgttaaagaa tctaatggtc   600
cactgcgcga acagcgccgc tggactccgg ctgaaaaaag gctttttttaa tgcagtcaga   660
ttcggcatcg gcatgtatgg ccttcgcccg tctgctgaca tgtcggacga gataccgttt   720
cagctgcgtc cggcatttac cctgcattcg acactgtcac atgtcaaact gatcagaaaa   780
ggcgagagcg tcagctacgg agccgagtac acagcggaaa aagacacatg gatcgggacg   840
gtgcctgtag gctatgcgga cggctggctc cgaaaattga aagggaccga catccttgtg   900
aagggaaaac gcctgaaaat tgccggccga atttgcattg accaatttat ggtggagctg   960
gatcaggaat atccgccggg cacaaaagtc acattaatag gccggcaggg ggatgaatat   1020
atttccatgg atgagattgc aggaaggctc gaaaccatta ctatgaggt ggcctgtaca  1080
ataagttccc gtgttccccg tatgtttttg gaaaatggga gtataatgga agtaagaaat   1140
cctttattgc aggtaaatat aagcaat                                      1167

SEQ ID NO: 20          moltype = AA   length = 289
FEATURE                Location/Qualifiers
source                 1..289
                       mol_type = protein
                       organism = synthetic construct
SEQUENCE: 20
MKHGIYYAYW EQEWAADYKR YVEKAAKLGF DILEVGAAPL PDYSAQEVKE LKKCADDNGI    60
QLTAGYGPAF NHNMGSSDPK IREEALQWYK RLFEVMAGLD IHLIGGALYS YWPVDFATAN   120
KEEDWKHSVE GMQILAPIAS QYGINLGMEV LNRFESHILN TSEEGVKFVT EVGMDNVKVM   180
LDTFHMNIEE SSIGDAIRHA GKLLGHFHTG ECNRMVPGKG RTPWREIGDA LREIEYDGTV   240
VMEPFVRMGG QVGSDIKVWR DISKGAGEDR LDEDARRAVE FQRYMLEWK               289

SEQ ID NO: 21          moltype = AA   length = 289
FEATURE                Location/Qualifiers
source                 1..289
                       mol_type = protein
                       organism = synthetic construct
SEQUENCE: 21
MKHGIYYSYW EHEWSAKFGT YIEKVAKLGF DIIEVAAHHI NEYSDAELAV IRQSAKDNGI    60
ILTAGIGPSK TKNLSSEDAA VRAAGKAFFE RTLTNVAKLD IHTIGGALHS YWPIDYSQPV   120
DKAGDYARGV EGIHGIADFA NDLGINLCIE VLNRFENHVL NTAAEGVAFV KDVGKNNVKV   180
MLDTFHMNIE EDSFGEAIRT AGPLLGHFHT GESNRRVPGK GRMPWHEIGL ALRDINYTGA   240
VVMEPFVKTG GTIGSDIKVW RDLSGGADLA KMDEDARNAL AFSRFVLGS               289

SEQ ID NO: 22          moltype = AA   length = 288
FEATURE                Location/Qualifiers
source                 1..288
                       mol_type = protein
                       organism = synthetic construct
SEQUENCE: 22
MKHGIYYAYW EKEWRGDYLY YIEKAARLGF DILELAASPF PEYSKEEIRA LRDCAKSNGI    60
```

-continued

```
ILTAGHGPSA DCNIASADPA VKANALEFYK KIFDVMEQLD IHTIGGGIYS YWPVDYTKPI   120
DIAGDWKRSV EGVREMADIA KDHGITLCLE VLNRFEGYLL NTSEEGTRFV KEVDKENVKV   180
MLDTFHMNIE ETSIGDAIRT AGKYLGHFHT GECNRLCPGK GRTPWREIHD ALHDIGYDRA   240
VVMEPFVQTG GTVGSDIKVW REMVPDLSEA KLDADAKDAL IFQRYMLD               288

SEQ ID NO: 23          moltype = AA  length = 289
FEATURE                Location/Qualifiers
source                 1..289
                       mol_type = protein
                       organism = synthetic construct
SEQUENCE: 23
MKHGIYYSYW EHEWSAKFGP YVEKVAKLGF DVIEVAAHHI NEYSDAELAE IRRTAKDNNI    60
ILTAGIGPSK TKNLSSPDIA VRQAGKAFFE QTLTNVAKLD IKTIGGALHS YWPVDYSKPI   120
DKEGDRARGV EGIHGIADFA GNLGINLCIE VLNRFENHVL NTAAEGVAFV KDVGKPNVKV   180
MLDTFHMNIE EDSFGEAIRT AGPLLGHFHT GESNRRVPGK GRMPWHEIGL ALRDISYAGA   240
VVMEPFVKTG GTIGSDIRVW RDLTDGADET KMDEDARNAL AFSRFVLGG              289
```

STRAIN PRODUCING D-ALLULOSE 3-EPIMERASE AND APPLICATION THEREOF

REFERENCE TO SEQUENCE LISTING

The instant application contains a Sequence Listing in XML format as a file named "YGHY-2022-66 SEQ.xml", created on Dec. 21, 2022, of 30 kB in size, and which is hereby incorporated by reference in its entirety.

TECHNICAL FIELD

The present disclosure relates to a strain producing D-allulose 3-epimerase and application thereof, and belongs to the technical field of bioengineering.

BACKGROUND

D-allulose, a C-3 epimer of D-fructose, can be used as a low-calorie sweetener, produce a pleasant flavor through the Maillard reaction, improve the gelatification of food, and regulate biological functions such as lowering blood sugar and blood lipid levels, reducing fat accumulation, and scavenging reactive oxygen species (ROS).

As early as 2014, the U.S. Food and Drug Administration's laws and regulations listed D-allulose as generally safe, allowing it to be added to foods, dietary supplements, and pharmaceutical preparations. Therefore, D-allulose has broad application prospects in the fields of medicine and food.

As a rare sugar, D-allulose exists in a very small amount in nature, and is unrealistic to be directly extracted. Meanwhile, chemical synthesis will produce by-products, causing difficulties in separation and greatly increasing production costs, and a complex reaction process can produce excessive pollution. Hence, the main method used is biotransformation for the production of D-allulose at present. Compared with natural extraction and chemical synthesis, biotransformation has the advantages of mild reaction conditions, high specificity, environmental friendliness, etc. In biotransformation, D-allulose 3-epimerase plays a key role in converting D-fructose to D-allulose.

*Bacillus subtilis* is a food grade microorganism (GRAS) suitable for industrial production. Also, *B. subtilis* has the advantages of being clear in genetic background, simple and mature in genetic manipulation, easy for large-scale expanded cultivation, etc., and is an advantageous platform for fermentative synthesis of D-allulose 3-epimerase.

SUMMARY

The first objective of the present disclosure is to provide an expression vector for enhancing the expression of a target protein, and the expression vector is obtained by replacing a P43 promoter on a pP43NMK plasmid with any one of a group of promoters consisting of hag, ylbP, hagP43, ylbPylbP, and haghag.

The nucleotide sequences of the promoters hag, ylbP, hagP43, ylbPylbP, and haghag are shown in SEQ ID NO. 2, SEQ ID NO. 3, SEQ ID NO. 4, SEQ ID NO. 5, and SEQ ID NO. 6, respectively.

In one implementation of the present disclosure, the target protein is D-allulose 3-epimerase or phosphorylated glycosyl epimerase, the amino acid sequence of the D-allulose 3-epimerase is shown in SEQ ID NO. 20 or SEQ ID NO. 21, and the amino acid sequence of the phosphorylated glycosyl epimerase is shown in SEQ ID NO. 22 or SEQ ID NO. 23.

In one implementation of the present disclosure, the nucleotide sequence encoding the D-allulose 3-epimerase is shown in SEQ ID NO. 1.

The second objective of the present disclosure is to provide an expression vector, which is obtained by replacing a P43 promoter on a pP43NMK plasmid with the hag promoter whose nucleotide sequence is shown in SEQ ID NO. 2, and simultaneously mutating the base positions 129 to 137 on the sequence of the hag promoter.

In one implementation of the present disclosure, an aggaggaa sequence in base positions 129 to 137 on a hag sequence of the nucleotide sequence shown in SEQ ID NO. 2 is mutated to: gaggaggaa (named R2), or ggggaggag (named R4), or agggaggag (named R11), or agggagggg (named R13), or aaggaggag (named R14), or aaggagggg (named R15).

The third objective of the present disclosure is to provide a non-antibiotic resistance expression vector, which is obtained by:

replacing a P43 promoter on a pP43NMK plasmid with a hag promoter whose nucleotide sequence is shown in SEQ ID NO. 2, and simultaneously mutating the base positions 129 to 137 on the sequence of the hag promoter to: ggggaggag; and replacing a resistance gene kanamycin Kan on the pP43NMK plasmid with an alanine racemase gene dal whose nucleotide sequence is shown in SEQ ID NO. 19; or replacing a P43 promoter on a pUB110 plasmid with a hag promoter whose nucleotide sequence is shown in SEQ ID NO. 2, and simultaneously mutating the base positions 129 to 137 on the sequence of the hag promoter to: ggggaggag; and replacing resistance genes kanamycin Kan and bleomycin Blm on the pUB110 plasmid with an alanine racemase gene dal whose nucleotide sequence is shown in SEQ ID NO. 19.

In one implementation of the present disclosure, the expression vector is a replicable plasmid pUB-hag-RBS4-dpe-dal replacing resistance genes kanamycin Kan and bleomycin Blm with alanine racemase gene dal as a selection marker, and a replicable plasmid pP43NMK-hag-RBS4-dpe-dal replacing resistance gene kanamycin Kan with alanine racemase gene dal as a selection marker.

In one implementation of the present disclosure, the nucleotide sequence of the alanine racemase gene dal is shown in SEQ ID NO. 19.

The third objective of the present disclosure is to provide a recombinant cell containing the above expression vector.

In one implementation of the present disclosure, the recombinant cell uses bacteria or fungi as expression hosts.

In one implementation of the present disclosure, the recombinant cell uses *B. subtilis* WB800 or *B. subtilis* 1A751 as an expression host.

The fourth objective of the present disclosure is to provide recombinant *B. subtilis*, which uses the above vector as an expression vector and *B. subtilis* WB800 or *B. subtilis* 1A751 as an expression host to express D-allulose 3-epimerase.

In one implementation of the present disclosure, the nucleotide sequence encoding the D-allulose 3-epimerase gene is shown in SEQ ID NO. 1.

The fifth objective of the present disclosure is to provide recombinant *B. subtilis*, which is obtained by transforming an expression vector carrying a target gene into *B. subtilis* with the alanine racemase gene knocked out. The expression vector is obtained by:

replacing a P43 promoter on a pP43NMK plasmid with a hag promoter whose nucleotide sequence is shown in SEQ ID NO. 2, and simultaneously mutating the base positions 129 to 137 on the sequence of the hag promoter to: ggggaggag; or replacing a P43 promoter on a pP43NMK plasmid with a hag promoter whose nucleotide sequence is shown in SEQ ID NO. 2, and simultaneously mutating the base positions 129 to 137 on the sequence of the hag promoter to: ggggaggag; and replacing a resistance gene kanamycin Kan on the pP43NMK plasmid with an alanine racemase gene dal whose nucleotide sequence is shown in SEQ ID NO. 19; or replacing a P43 promoter on a pUB110 plasmid with a hag promoter whose nucleotide sequence is shown in SEQ ID NO. 2, and simultaneously mutating the base positions 129 to 137 on the sequence of the hag promoter to: ggggaggag; and replacing resistance genes kanamycin Kan and bleomycin Blm on the pUB110 plasmid with an alanine racemase gene dal whose nucleotide sequence is shown in SEQ ID NO. 19.

In one implementation of the present disclosure, the recombinant *B. subtilis* uses *B. subtilis* 1A751, *B. subtilis* WB600 or *B. subtilis* WB800 with the alanine racemase gene knocked out as an expression host.

In one implementation of the present disclosure, the expression host is: *B. subtilis* 1A751, and the *B. subtilis* with the alanine racemase gene knocked out is: *B. subtilis* 1A751Δdal.

In one implementation of the present disclosure, the *B. subtilis* 1A751Δdal used in the present disclosure, i.e., *B. subtilis* 1A751 with the D-alanine racemase gene dal on the chromosome knocked out, was constructed in the early stage of the laboratory. (Construction method, refer to the patent: Jiang Bo, Mu Wanmeng, He Weiwei, Zhang Tao. Construction Method of Non-antibiotic Resistance Gene Chromosome Integrated Recombinant *B. subtilis* Expressing D-allulose 3-epimerase Based on Cre/lox System: the Chinese invention patent application text with publication number CN104946577A).

The sixth objective of the present disclosure is to provide a method for increasing the expression of D-allulose 3-epimerase, and the method uses the above expression vector for expression.

The seventh objective of the present disclosure is to provide a method for producing D-allulose 3-epimerase, and the method comprises: obtaining bacterial cells of recombinant *B. subtilis* carrying D-allulose 3-epimerase, and isolating D-allulose 3-epimerase from the bacterial cells.

The eighth objective of the present disclosure is to provide a method for producing D-allulose, and the method comprises: adding the prepared recombinant D-allulose 3-epimerase to a reaction system containing fructose for reaction to obtain a reaction solution, and isolating D-allulose from the reaction solution.

In one implementation of the present disclosure, in the fermentation broth of the recombinant cell or recombinant *B. subtilis*, the enzyme activity of the recombinant D-allulose 3-epimerase is at least 15.67 U/mL.

The ninth objective of the present disclosure is to provide application of the above recombinant *B. subtilis* carrying D-allulose 3-epimerase in preparation of D-allulose or products containing same.

In one implementation of the present disclosure, the products comprise foods, drugs or cosmetics.

Beneficial Effects (1) The present disclosure provides a method for improving the expression of D-allulose 3-epimerase by screening promoters and optimizing RBS thereof. The recombinant *B. subtilis* constructed using the vectors pP43NMK-hag and pP43NMK-hag-RBS4 provided by the present disclosure improves the enzyme activity of the target gene D-allulose 3-epimerase, and the enzyme activities upon transformation are 1.30 times and 1.69 times that of the original pP43NMK-P43/*B. subtilis* WB800, and 1.77 times and 2.29 times that of pP43NMK-HpaII/*B. subtilis* WB800.

(2) The present disclosure provides food-grade recombinant *B. subtilis* expressing D-allulose 3-epimerase, which is safer and more suitable for industrial production of D-allulose compared with general host strains.

DETAILED DESCRIPTION

The pP43NMK plasmid involved in the following examples was purchased from Miaoling Bio. The *Escherichia coli* DH5α involved in the following examples was purchased from General Biotechnology Co., Ltd. The *B. subtilis* WB800 involved in the following examples was purchased from the NTCC Center for Type Culture Collection.

The *B. subtilis* 1A751Δdal involved in the following examples, i.e., *B. subtilis* 1A751 with the D-alanine racemase gene dal on the chromosome knocked out, was constructed by a method referring to patent: Jiang Bo, Mu Wanmeng, He Weiwei, Zhang Tao. Construction Method of Non-antibiotic Resistance Gene Chromosome Integrated Recombinant *B. subtilis* Expressing D-allulose 3-epimerase Based on Cre/lox System [P]: the Chinese invention patent application text with publication number CN104946577A.

For the D-allulose 3-epimerase involved in the following examples, the present disclosure only takes D-allulose 3-epimerase whose nucleotide sequence is shown in SEQ ID NO. 1 as an example to illustrate the technical effects of the present disclosure, but not to limit the examples of the present disclosure. It should be noted that the D-allulose 3-epimerase whose amino acid sequence is shown in SEQ ID NO. 20 or SEQ ID NO. 21 in the present disclosure, or the sequence after codon optimization, or mutation transformation may still achieve the technical effects of the present disclosure.

Culture Mediums Involved in the Following Examples are as Follows:

LB liquid medium: tryptone 10 g/L, yeast extract 5 g/L, and sodium chloride 10 g/L, natural pH.

LB solid medium: tryptone 10 g/L, yeast extract 5 g/L, sodium chloride 10 g/L, and agar powder 15 g/L.

Fermentation medium: glucose 15 g/L, yeast extract 20 g/L, sodium chloride 8 g/L, disodium hydrogen phosphate dodecahydrate 1 g/L, and magnesium sulfate heptahydrate 1 g/L, pH 7.0.

Detection Methods Involved in the Following Examples are as Follows:

Enzyme activity assay method for D-allulose 3-epimerase: adding 800 μl of D-fructose (100 g/L) dissolved in a phosphate buffer (50 mM, pH 7.0) and 200 μL of fermentation broth to a 1 mL reaction system, preserving heat at 55° C. for 10 min, and boiling the reaction system for 10 min to stop the enzyme reaction.

Detecting the yield of D-allulose by HPLC, and calculating the enzyme activity. Definition of enzyme activity unit (U): The amount of enzyme required to catalyze the production of 1 μmol of D-allulose per minute is one enzyme activity unit.

Enzyme activity (U/mL)=Amount of allulose produced in the reaction system (mg/mL)*1 mL*1000/180/10/0.2.

Example 1: Construction of Recombinant *B. subtilis* Containing Different Promoters Specific operation steps are as follows:

(1) Obtainment of D-allulose 3-epimerase gene: The artificially synthesized nucleotide sequence was shown in SEQ ID NO. 1.

(2) Obtainment of different promoter genes: The promoters used included hag, ylbP, hagP43, ylbPylbP, haghag, amyE, aprE, gsiB, Hpall, nprE, sigX, P43hag, ylbPhag, hagylbP, ylbPP43, P43ylbP, and P43P43, whose nucleotide sequences were shown in SEQ ID NO. 2 to SEQ ID NO. 18, respectively.

Among the single promoters, except that Hpall cloned with a PMA5 plasmid as the template, other single promoters were PCR amplified with *B. subtilis* 168 as the template. The double promoters were obtained by fusion PCR amplification by using a vector containing a single promoter as the template.

(3) The gene of D-allulose 3-epimerase was fused with the genes of the promoters by fusion PCR, and then the fused fragments were ligated with the linearized pP43NMK plasmids from which the gene of the P43 promoter was removed by homologous recombinase Exnase II to obtain ligated products. The ligated products were transformed into *E. coli* DH5a competent cells. The transformed *E. coli* DH5a competent cells were spread on LB solid mediums (containing 100 μg·mL$^{-1}$ ampicillin), and incubated upside down at 37° C. for 12 h. Positive transformants were picked, and the plasmids were extracted and verified by sequencing. The recombinant plasmids pP43NMK-Promoter-dpe were obtained if the verification was correct. The obtained recombinant plasmids pP43NMK-Promoter-dpe were transformed into *B. subtilis* WB800 competent cells to obtain transformed products. The transformed products were spread on an LB solid mediums (containing 100 μg·mL$^{-1}$ kanamycin), and incubated upside down in a constant temperature incubator at 37° C. for 12 h to obtain transformants. The transformants were verified by PCR, and the recombinant strains *B. subtilis* were obtained if the verification was correct.

The obtained *B. subtilis* strains were as follows: *B. subtilis* WB800/pP43NMK-hag-dpe, *B. subtilis* WB800/pP43NMK-ylbP-dpe, *B. subtilis* WB800/pP43NMK-hagP43-dpe, *B. subtilis* WB800/pP43NMK-ylbPylbP-dpe, *B. subtilis* WB800/pP43NMK-haghag-dpe, *B. subtilis* WB800/pP43NMK-amyE-dpe, *B. subtilis* WB800/pP43NMK-aprE-dpe, *B. subtilis* WB800/pP43NMK-gsiB-dpe, *B. subtilis* WB800/pP43NMK-Hpall-dpe, *B. subtilis* WB800/pP43NMK-nprE-dpe, *B. subtilis* WB800/pP43NMK-sigX-dpe, *B. subtilis* WB800/pP43NMK-P43hag-dpe, *B. subtilis* WB800/pP43NMK-ylbPhag-dpe, *B. subtilis* WB800/pP43NMK-hagylbP-dpe, *B. subtilis* WB800/pP43NMK-ylbPP43-dpe, *B. subtilis* WB800/pP43NMK-P43ylbP-dpe, *B. subtilis* WB800/pP43NMK-P43P43-dpe.

Example 2: Fermentative Production of D-Allulose 3-Epimerase by Promoter-Containing Recombinant *B. subtilis*

Specific steps are as follows:

(1) The recombinant strains *B. subtilis* prepared in Example 1 were added to LB liquid mediums respectively, and incubated on a shaker at 37° C. and 200 rpm for 12 h to obtain seed liquids.

(2) The prepared seed liquids were transferred into fermentation mediums according to an inoculum concentration of 3% (v/v), and incubated on a shaker at 37° C. and 200 rpm. Enzyme-containing bacterial cells were isolated.

Figure 1:
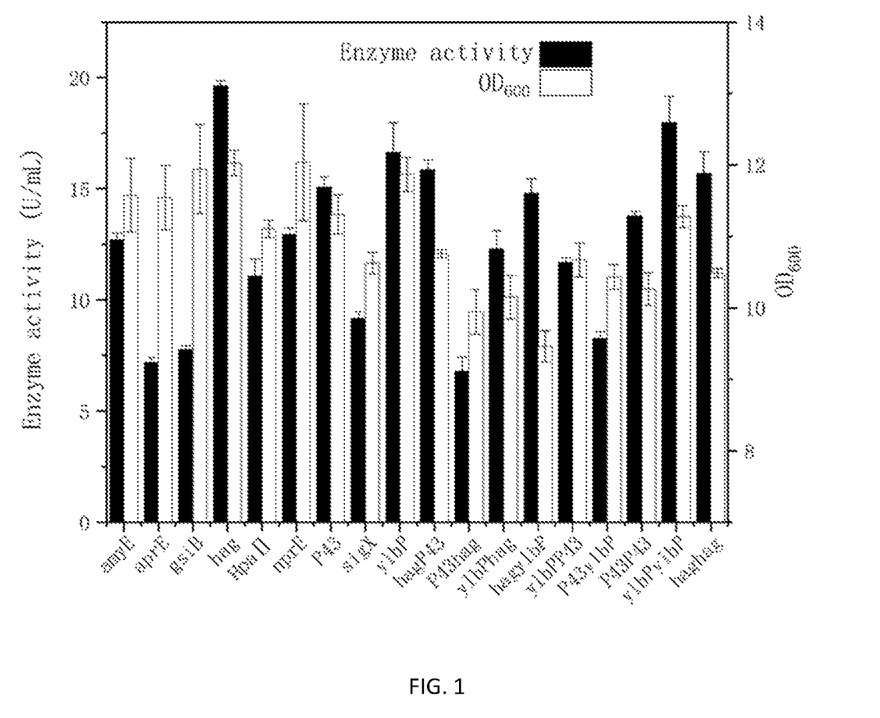
FIG. 1 shows the enzyme activities and $OD_{600}$ values of recombinant strains containing different promoters in shake flasks.

The enzyme activities of D-allulose 3-eimerase in the bacterial cells of the fermentation broths were detected respectively, and the results were shown in Table 1 and FIG. 1.

TABLE 1

Enzyme activities of D-allulose 3-epimerase prepared by different recombinant strains *B. subtilis*

| Recombinant strains | Fermentation enzyme activity (U/mL fermentation broth) |
|---|---|
| *B. subtilis* WB800/pP43NMK-P43-dpe | 15.05 |
| *B. subtilis* WB800/pP43NMK-hag-dpe | 19.62 |
| *B. subtilis* WB800/pP43NMK-ylbP-dpe | 16.62 |
| *B. subtilis* WB800/pP43NMK-hagP43-dpe | 15.84 |
| *B. subtilis* WB800/pP43NMK-ylbPylbP-dpe | 17.95 |
| *B. subtilis* WB800/pP43NMK-haghag-dpe | 15.67 |
| *B. subtilis* WB800/pP43NMK-amyE-dpe | 12.71 |
| *B. subtilis* WB800/pP43NMK-aprE-dpe | 7.18 |
| *B. subtilis* WB800/pP43NMK-gsiB-dpe | 7.76 |
| *B. subtilis* WB800/pP43NMK-Hpall-dpe | 11.06 |
| *B. subtilis* WB800/pP43NMK-nprE-dpe | 12.93 |
| *B. subtilis* WB800/pP43NMK-sigX-dpe | 9.16 |
| *B. subtilis* WB800/pP43NMK-P43hag-dpe | 6.78 |
| *B. subtilis* WB800/pP43NMK-ylbPhag-dpe | 11.66 |
| *B. subtilis* WB800/pP43NMK-hagylbP-dpe | 14.79 |
| *B. subtilis* WB800/pP43NMK-ylbPP43-dpe | 11.66 |
| *B. subtilis* WB800/pP43NMK-P43ylbP-dpe | 8.24 |
| *B. subtilis* WB800/pP43NMK-P43P43-dpe | 13.77 |

The results show that the effect of the recombinant strain *B. subtilis* WB800/pP43NMK-hag-dpe is the best, and the enzyme activity is as high as 19.62 U/mL.

Therefore, in subsequent examples, the plasmid pP43NMK-hag-dpe was used as a template, and the RBS sequence on the hag promoter was mutated to further improve the enzyme activity of D-allulose 3-epimerase.

Example 3: Construction of Recombinant *B. subtilis* Containing Different RBSs Specific steps are as follows:

Using the plasmid pP43NMK-hag-dpe as a template and RBS-F/RBS-R as primers, one-step PCR was performed to mutate the RBS sequence on the hag promoter to construct linearized plasmids containing different RBS sequences.

The primers were as follows:
RBS-F: tgccttaacaacatattcrrggaggrrcaaaacaatgaagcatggta
RBS-R: taccatgcttcattgttttgyycctccyygaatatgttgttaaggca The constructed linearized plasmids were transformed into *E. coli* DH5a competent cells. The transformed *E. coli*

DH5a competent cells were spread on LB solid mediums (containing 100 μg·mL⁻¹ ampicillin), and incubated upside down at 37° C. for 12 h. A certain number of positive transformants were picked, and the plasmids were extracted and verified by sequencing. The recombinant plasmids pP43NMK-hag-RBSn-dpe were obtained if the verification is correct. 15 different RBS mutants were obtained, and the mutant sequences were as follows:

ggggaggaa (named R1), gaggaggaa (named R2), ggggaggga (named R3), ggggaggag (named R4), gaggagggg (named R5), gaggaggga (named R6), ggggagggg (named R7), gaggaggag (named R8), aaggaggaa (named R9), agggagga (named R10), agggaggag (named R11), aaggaggga (named R12), agggagggg (named R13), aaggaggag (named R14), and aaggagggg (named R15).

The obtained recombinant plasmids were as follows:
pP43NMK-hag-R1-dpe, pP43NMK-hag-R2-dpe, pP43NMK-hag-R3-dpe, pP43NMK-hag-R4-dpe, pP43NMK-hag-R5-dpe, pP43NMK-hag-R6-dpe, pP43NMK-hag-R7-dpe, pP43NMK-hag-R8-dpe, pP43NMK-hag-R9-dpe, pP43NMK-hag-R10-dpe, pP43NMK-hag-R11-dpe, pP43NMK-hag-R12-dpe, pP43NMK-hag-R13-dpe, pP43NMK-hag-R14-dpe, pP43NMK-hag-R15-dpe.

The unmutated RBS sequence is named R0, and the recombinant plasmid may be expressed as: pP43NMK-hag-R0-dpe.

The obtained recombinant plasmids pP43NMK-hag-Rn-dpe and pP43NMK-hag-R0-dpe were transformed into *B. subtilis* WB800 competent cells respectively to obtain transformed products. The transformed products were spread on LB solid mediums (containing 100 μg·mL⁻¹ kanamycin), and incubated upside down in a constant temperature incubator at 37° C. for 12 h to obtain transformants. The transformants were sequenced, and the recombinant strains *B. subtilis* were obtained if the verification is correct.

That is, the obtained recombinant strains *B. subtilis* were as follows:
*B. subtilis* WB800/pP43NMK-hag-R1-dpe, *B. subtilis* WB800/pP43NMK-hag-R2-dpe, *B. subtilis* WB800/pP43NMK-hag-R3-dpe, *B. subtilis* WB800/pP43NMK-hag-R4-dpe, *B. subtilis* WB800/pP43NMK-hag-R5-dpe, *B. subtilis* WB800/pP43NMK-hag-R6-dpe, *B. subtilis* WB800/pP43NMK-hag-R7-dpe, *B. subtilis* WB800/pP43NMK-hag-R8-dpe, *B. subtilis* WB800/pP43NMK-hag-R9-dpe, *B. subtilis* WB800/pP43NMK-hag-R10-dpe, *B. subtilis* WB800/pP43NMK-hag-R11-dpe, *B. subtilis* WB800/pP43NMK-hag-R12-dpe, *B. subtilis* WB800/pP43NMK-hag-R13-dpe, *B. subtilis* WB800/pP43NMK-hag-R14-dpe, *B. subtilis* WB800/pP43NMK-hag-R15-dpe, *B. subtilis* WB800/pP43NMK-hag-R0-dpe.

Example 4: Fermentation of Recombinant *B. subtilis* Containing Different RBSs Specific steps are as follows:

(1) The transformants of the recombinant *B. subtilis* prepared in Example 3 were streaked on LB solid mediums (containing 100 μg·mL⁻¹ kanamycin), and incubated upside down in a constant temperature incubator at 37° C. for 12 h to obtain single colonies.

(2) The single colonies were picked and transferred into LB liquid mediums (containing 100 μg·nL⁻¹ kanamycin), and incubated at 37° C. and 200 r/min for 12 h to obtain seed liquids.

(3) The prepared seed liquids were transferred into fermentation mediums at an inoculum concentration of 3% (v/v), and incubated at 37° C. and 200 r/min for 12 h or more to obtain fermentation broths.

Figure 2:
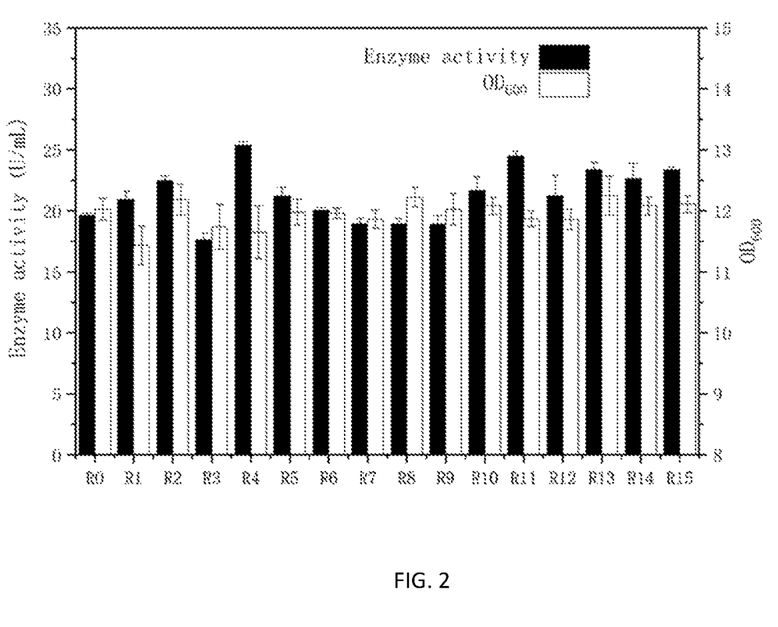
FIG. 2 shows the enzyme activities and $OD_{600}$ values of RBS mutant strains in shake flasks.

(4) The enzyme activities of D-allulose 3-eimerase prepared by the recombinant strains *B. subtilis* in the above fermentation broths were detected respectively. The results are shown in Table 2 and FIG. 2.

TABLE 2

Enzyme activity of D-allulose 3-epimerase prepared by recombinant strains *B. subtilis* containing different RBSs

| Recombinant strains | Fermentation enzyme activity (U/mL) |
|---|---|
| *B. subtilis* WB800/pP43NMK-hag-R1-dpe | 20.95 |
| *B. subtilis* WB800/pP43NMK-hag-R2-dpe | 22.49 |
| *B. subtilis* WB800/pP43NMK-hag-R3-dpe | 17.59 |
| *B. subtilis* WB800/pP43NMK-hag-R4-dpe | 25.39 |
| *B. subtilis* WB800/pP43NMK-hag-R5-dpe | 21.19 |
| *B. subtilis* WB800/pP43NMK-hag-R6-dpe | 20.02 |
| *B. subtilis* WB800/pP43NMK-hag-R7-dpe | 18.93 |
| *B. subtilis* WB800/pP43NMK-hag-R8-dpe | 18.89 |
| *B. subtilis* WB800/pP43NMK-hag-R9-dpe | 18.88 |
| *B. subtilis* WB800/pP43NMK-hag-R10-dpe | 21.66 |
| *B. subtilis* WB800/pP43NMK-hag-R11-dpe | 24.46 |
| *B. subtilis* WB800/pP43NMK-hag-R12-dpe | 21.25 |
| *B. subtilis* WB800/pP43NMK-hag-R13-dpe | 23.35 |
| *B. subtilis* WB800/pP43NMK-hag-R14-dpe | 22.64 |
| *B. subtilis* WB800/pP43NMK-hag-R15-dpe | 23.35 |
| *B. subtilis* WB800/pP43NMK-hag-R0-dpe | 19.62 |

The results show that the effect of the recombinant strain *B. subtilis* WB800/pP43NMK-hag-R4-dpe is the best, and the enzyme activity of D-allulose 3-eimerase is as high as 25.39 U/mL.

In addition, the enzyme activity of D-allulose 3-epimerase prepared by fermentation of the recombinant strain *B. subtilis* WB800/pP43NMK-hag-R2-dpe is 22.49 U/mL;

the enzyme activity of D-allulose 3-epimerase prepared by fermentation of the recombinant strain *B. subtilis* WB800/pP43NMK-hag-R11-dpe is 24.46 U/mL;

the enzyme activity of D-allulose 3-epimerase prepared by fermentation of the recombinant strain *B. subtilis* WB800/pP43NMK-hag-R13-dpe is 23.35 U/mL;

the enzyme activity of D-allulose 3-epimerase prepared by fermentation of the recombinant strain *B. subtilis* WB800/pP43NMK-hag-R14-dpe is 22.64 U/mL; and the enzyme activity of D-allulose 3-epimerase prepared by fermentation of the recombinant strain *B. subtilis* WB800/pP43NMK-hag-R15-dpe is 23.35 U/mL.

Example 5: Preparation of Non-Antibiotic Resistance Recombinant Vector

Specific operation steps are as follows:

(1) Obtainment of alanine racemase gene: The artificially synthesized nucleotide sequence was shown in SEQ ID NO. 19.

(2) Preparation of PUB-hag-RBS4-dpe-dal vector:

Using the PUB-P43-dpe-dal plasmid (constructed by a method described in the Chinese invention patent text with publication number CN104894047B) as a template, a linearized vector without the P43 gene was amplified by PCR. Using the pP43NMK-hag-R4-dpe plasmid constructed in Example 3 as a template, the hag-RBS4-dpe gene therein was amplified by PCR. The linearized vector and the target gene were ligated with high-fidelity polymerase Phata Max Super-Fidelity DNA Polymerase by a homology arm recombination principle.

(3) Preparation of pP43NMK-hag-RBS4-dpe-da/vector:

Using the pP43NMK-hag-R4-dpe plasmid constructed in Example 3 as a template, the linearized vectors except the resistance gene kanamycin Kan were amplified by PCR. Using the PUB-P43-dpe-dal plasmid constructed in the early stage of the laboratory as a template, the alanine racemase gene was amplified by PCR. The linearized vector and the target gene were ligated with high-fidelity polymerase Phata Max Super-Fidelity DNA Polymerase by a homology arm recombination principle.

(4) The reaction system and reaction conditions for ligation in step (2) and step (3) were as follows:

| Reaction system: | |
| --- | --- |
| Reagents | 50 μL reaction system (μL) |
| Phata Max Super-Fidelity DNA Polymerase | 1 |
| Vector fragment (100 ng/μL) | 2 |
| Target gene (100 ng/μL) | 2 |
| dNTP | 1 |
| Buffer (2×) | 25 |
| ddH$_2$O | up to 50 uL |

| Reaction conditions: | | |
| --- | --- | --- |
| Steps | Temperature (° C.) | Time |
| Predenaturation | 98 | 30 s-3 min |
| Denaturation | 98 | 5-10 s |
| Annealing | 45-72 | 10-30 s |
| Extension | 72 | 4-6 kb/min |
| Final extension | 72 | 5-10 min |

Denaturation-annealing-final extension was performed for a total of 25-35 cycles.

(5) The PCR products (multimer fragments) obtained in step (2) and step (3) were transformed into *B. subtilis* 1A751Δdal competent cells to obtain transformed products. The transformed products were spread on antibiotic-free LB solid mediums, and incubated upside down in a constant temperature incubator at 37° C. for 12 h to obtain transformants. The transformants were verified by PCR, and the non-antibiotic resistance recombinant strains *B. subtilis*, i.e., *B. subtilis* 1A751Δdal/PUB-hag-RBS4-dpe-dal, and *B. subtilis* 1A751Δdal/P43NMK-hag-RBS4-dpe-dal, were obtained if the verification was correct.

Example 6: Fermentative Preparation of D-Allulose 3-Epimerase with Non-Antibiotic Resistance Recombinant *B. subtilis*

Specific steps are as follows:

(1) The recombinant strains *B. subtilis* 1A751Δdal/PUB-hag-RBS4-dpe-dal and *B. subtilis* 1A751Δdal/pP43NMK-hag-RBS4-dpe-dal obtained in Example 3 were streaked on antibiotic-free LB solid mediums, and incubated upside down in a 37° C. constant temperature incubator for 12 h to obtain single colonies.

(2) The single colonies were picked and transferred into antibiotic-free LB liquid mediums and incubated at 37° C. and 200 r/min for 12 h to obtain seed liquids.

(3) The prepared seed liquids were transferred into antibiotic-free fermentation mediums at an inoculum concentration of 3% (v/v), and incubated at 37° C. and 200 r/min for 12 h or more to obtain fermentation broths.

(4) The enzyme activities of D-allulose 3-eimerase prepared by the recombinant strains *B. subtilis* were detected respectively. The results are shown in Table 3.

TABLE 3

Enzyme activities of D-allulose 3-epimerase prepared by non-antibiotic resistance recombinant strains *B. subtilis* containing different vectors

| Recombinant strains | Fermentation enzyme activity (U/mL) |
| --- | --- |
| *B. subtilis* 1A751-dal⁻/pP43NMK-hag-RBS4-dpe-dal | 24.72 |
| *B. subtilis* 1A751-dal⁻/PUB-hag-RBS4-dpe-dal | 19.13 |

The results show that the enzyme production effect of the non-antibiotic resistance recombinant strain *B. subtilis* 1A751-dal/pP43NMK-hag-RBS4-dpe-dal is the best, and the highest fermentation enzyme activity is 24.72 U/mL.

Therefore, the present disclosure may realize fermentative preparation of D-allulose 3-epimerase with food-grade strains in an antibiotic-free culture medium.

Example 7: Fermentative Preparation of D-Allulose 3-Epimerase (1) The single colonies of the non-antibiotic resistance recombinant strain *B. subtilis* 1A751-dal/pP43NMK-hag-RBS4-dpe-dal on a plate were picked and transferred into 50 mL (with a liquid volume in flask of 10%) of LB liquid medium, and incubated on a shaker at 37° C. and 200 r/min for 12 h to obtain a seed liquid.

(2) A fermentation medium was put in a 3 L fermenter, and the seed liquid obtained in step (1) was transferred into the fermentation medium at an inoculum concentration of 3% (v/v) for fermentation incubation with the ventilation rate and stirring rate being continuously adjusted during fermentation to ensure that the DO value was controlled at 30% and the fermentation temperature was 37° C.

(3) When the dissolved oxygen began to increase, a feeding medium containing glucose (200 g/L) and magnesium sulfate heptahydrate (5 g/L) was fed at a feeding rate controlled at 40 mL/h.

(4) During feeding, the enzyme activity was detected at any time, and the fermentation was stopped when the enzyme activity began to decrease after feeding. The detected fermentation enzyme activity of D-allulose 3-epimerase was 714.8 U/mL.

(5) The fermented bacterial cells were centrifugally separated, and the enzyme activity of the obtained wet bacterial cells containing D-allulose 3-epimerase was 13612.5 U/g.

Example 8: Preparation of D-Allulose

A substrate D-fructose solution (with a concentration of 45%) was added to a 1000 mL jacketed enzyme reactor, the reaction temperature was kept at 55° C., and the pH was adjusted to 7.0. The bacterial cells containing D-allulose 3-eimerase prepared in Example 7 was added to fructose according to 30 U/g fructose, and reacted under stirring at a rotating speed of 100 r/min.

During the reaction, the reaction solution was sampled, boiled to kill the enzyme, and centrifuged to obtain the supernatant, and the content of D-allulose was detected by HPLC assay.

After 8 h of reaction, the whole reaction reached an equilibrium state, and the conversion rate of D-allulose was 28.5%.

Although the present disclosure has been disclosed as above in preferred examples, it is not intended to limit the present disclosure. Anyone familiar with this technology can make various changes and modifications without departing from the spirit and scope of the present disclosure. Therefore, the protection scope of the present disclosure should be defined by the claims.

What is claimed is:

1. A recombinant *Bacillus subtilis* (*B. subtilis*), obtained by transforming with an expression vector carrying a target gene D-allulose 3-epimerase into *B. subtilis* with an alanine racemase gene knocked out, the expression vector being obtained by:

replacing a P43 promoter on a pP43NMK plasmid carrying a D-allulose 3-epimerase gene with a hag promoter whose nucleotide sequence is set forth in SEQ ID NO. 2, and simultaneously mutating the base positions 129 to 137 on the sequence of the hag promoter to: ggggaggag; and replacing a resistance gene kanamycin Kan on the pP43NMK plasmid with an alanine racemase gene dal whose nucleotide sequence is set forth in SEQ ID NO. 19; or replacing a P43 promoter on a pUB110 plasmid carrying a D-allulose 3-epimerase gene with a hag promoter whose nucleotide sequence is set forth in SEQ ID NO. 2, and simultaneously mutating the base positions 129 to 137 on the sequence of the hag promoter to: ggggaggag;

and replacing resistance genes kanamycin Kan and bleomycin Blm on the pUB110 plasmid with an alanine racemase gene dal whose nucleotide sequence is set forth in SEQ ID NO. 19.

2. The recombinant *B. subtilis* according to claim 1, wherein the recombinant *B. subtilis* uses *B. subtilis* 1A751 with the alanine racemase gene knocked out as an expression host.

3. The recombinant *B. subtilis* according to claim 1, wherein the recombinant *B. subtilis* uses *B. subtilis* WB600 with the alanine racemase gene knocked out as an expression host.

4. The recombinant *B. subtilis* according to claim 1, wherein the recombinant *B. subtilis* uses *B. subtilis* WB800 with the alanine racemase gene knocked out as an expression host.

* * * * *